United States Patent [19]

Chaplits

[11] 4,012,456
[45] Mar. 15, 1977

[54] METHOD FOR SEPARATION OF ISOBUTYLENE FROM C$_4$ HYDROCARBON FRACTIONS

[76] Inventor: Donat Nikolaevich Chaplits, ulitsa Pervomaiskaya, 9, kv. 36, Yaroslavl, U.S.S.R.

[22] Filed: Nov. 19, 1974

[21] Appl. No.: 525,113

[52] U.S. Cl. ............................. 260/677 A; 260/641
[51] Int. Cl.$^2$ ........................................ C07C 11/08
[58] Field of Search ............ 260/677 A, 677 R, 641

[56] References Cited

UNITED STATES PATENTS

| | | | |
|---|---|---|---|
| 2,891,999 | 6/1959 | Langer | 260/641 |
| 3,256,250 | 6/1966 | Frilette | 260/641 |
| 3,328,471 | 6/1967 | Krönig | 260/641 |
| 3,397,250 | 8/1968 | Nambu | 260/677 R |
| 3,527,829 | 9/1970 | Horie et al. | 260/641 |
| 3,823,198 | 7/1974 | Goldsby | 260/677 A |
| 3,864,419 | 2/1975 | Murphy | 260/677 A |

OTHER PUBLICATIONS

Product Research and Development "Direct Hydration of Propylene over Ion-Exchange Resin," Kaises et al., vol. 1, Dec. 1962.

*Primary Examiner*—Herbert Levine

[57] ABSTRACT

The method for separation of isobutylene from hydrocarbon fractions containing four carbon atoms consists in processing said hydrocarbon fractions with water at a temperature of 70°–110° C and a pressure of 16 – 23 atmospheres, at a molar ratio of the said hydrocarbon fractions to water of 1:5–20, in the presence of a polar solvent taken in the quantity of 10–70 per cent of the weight of water, and also in the presence of a catalyst. The resultant reaction mixture contains tertiary butyl alcohol and water. Tertiary butyl alcohol is isolated from the reaction mixture as its aqueous solution and is dehydrated at a temperature of 80°–110° C and a pressure not above 3 atm, in the presence of the same catalyst. The catalyst, that is used at the stage of processing the hydrocarbon fractions with water, and also at the step of dehydration of tertiary butyl alcohol, is a moulded ion-exchange catalyst consisting of a sulphonated copolymer of styrene with divinylbenzene or diisopropenylbenzene, and a sulphonated thermoplastic material, for example, sulfonated-polyethylene, -polypropylene and -polyvinyl chloride, taken in the weight ratio of 1–4:1–2, of sulfonated styrene-dialkenylbenzene copolymer:sulfonated thermoplastic material, respectively.

2 Claims, No Drawings

METHOD FOR SEPARATION OF ISOBUTYLENE FROM C₄ HYDROCARBON FRACTIONS

This invention relates to methods for separation of isobutylene from hydrocarbon fractions having four carbon atoms.

The method of preparing the molded ion-exchange catalyst which is employed in the present invention is disclosed in U.S. patent application Ser. No. 525,115, filed on Nov. 19, 1974 now U.S. Pat. No. 3,965,039.

Isobutylene is widely used in synthesis of butyl rubber, in oil refining and petrochemical industries for preparing polyisobutylene, stabilizing additives to oils, fuels, and other products in organic synthesis of methylallyl chloride, and other products.

Known in the prior art is the method for recovery of isobutylene from $C_4$ hydrocarbon fractions with the use of sulphocationites, i.e., sulfonated polystyrene cation exchange resins. The method consists in that a hydrocarbon fraction having four carbon atoms is mixed with water at a molar ratio of 1 : 10–20 in the presence of a polar solvent (25–50 percent of the weight of water), for example ethyl 'Cellosolve'. The process can be realized also in the presence of a non-ionic emulsifying agent, for example, hydroxyethylated alkylphenol (1 percent of the weight of water). The prepared liquid mixture is delivered for hydration into the reaction vessel at a space velocity of $1.5 - 2.1$ hour$^{-1}$. The linear velocity of the liquid passage through the reactor is 10 – 15 m/hour. A sulphocationite, for example one of the addition polymerization type, is arranged in the reactor in beds to a height of about 1.5–2.0 meters each. Isobutylene is hydrated in the reaction vessel at a temperature of 85°–90° C and a pressure of 16–20 atm into tertiary butyl alcohol. The process occurs in the liquid phase. The conversion of isobutylene is 85–95 percent. From the reaction vessel, the reaction mixture containing tertiary butyl alcohol and water is delivered into an intermediate vessel.

The reaction mixture is heated to evaporate unreacted hydrocarbons, and tertiary butyl alcohol is concentrated by rectification. The result of this process is a solution of tertiary butyl alcohol in water (85–88 percent concentration). The solution is delivered into a dehydrator which is a vertical cylindrical apparatus consisting of the reaction and rectification parts. The upper, or reaction part, is filled with condensation type sulphocation exchange material in the form of granules of irregular shape sizing 0.3–1.3 mm. The height of the cation exchange bed is 2.2 m. The sulphocationite is loaded into the apparatus on special packs of gauze. The lower, or rectification part of the column, is packed with cap trays. The concentrated agueous solution of tertiary butyl alcohol is delivered into the middle part of the reactor, in the zone below the catalyst bed, at a space velocity of 0.3–0.5 hour$^{-1}$. The dehydration of alcohol is effected at a temperature of 80°–110° C at a pressure not above 3 atm, preferably at 0.5–0.9 atm. The dehydrated product, which is gaseous isobutylene containing admixtures of vapours of unreacted tertiary butyl alcohol, is condensed and withdrawn from the system. Alcohol is condensed and returned into the upper part of the reactor. The linear velocity of gas and vapour in the reaction part of the reactor is 0.1 m/sec. The other product of the dehydration process — water containing admixtures of tertiary butyl alcohol — is delivered into the rectification part of the reactor from which gaseous tertiary butyl alcohol is delivered into the reaction part of the reactor, while water is withdrawn from the system. The conversion of tertiary butyl alcohol is 97 percent.

Sulphocation exchange material is used in the form of small granules. The bed of such granules produces high hydraulic resistance to the flow of the reacting components, which interferes with the pre-determined conditions of the process. Moreover, in the hydrator, where the components move in a down-stream flow, the sulphocationite cakes into hard formations and the resistance to the reagent flow thus increases. In the dehydrator, where the vapour and liquid pass in counter-current flows, owing to the high hydraulic resistance, the cation exchange polymerization resins in the form of spherical granules sizing from 0.3 to 0.8 mm and having high catalytic activity and thermal stability (as compared with the condensation type sulphocationites) cannot be used at all. The application of the polymerization type sulphocationites leads to "flooding" of the catalyst bed. The production capacity of the process is thus strongly deteriorated.

Making use of sulphocationites in industrial conditions requires complicated equipment, especially the dehydrator, since otherwise the catalyst is washed out from the reactor, and the reaction products are distributed over the catalyst bed in a non-uniform manner. The sulphocationite bed height in the hydrator, as well as in the dehydrator, does not exceed 2 meters.

The object of this invention is to develop a method for separation of isobutylene from hydrocarbon fractions having four carbon atoms, that would provide for the higher production capacity and would be simple to realize.

In accordance with this and other objects, the invention consists in that proposed is a method for separation of isobutylene from $C_4$ hydrocarbon fractions consisting in that said fractions are processed with water at a temperature of 70°–110° C at a pressure of 16–23 atm, at a molar ratio of the hydrocarbon fractions to water of 1 : 5–20, in the presence of a polar solvent taken in the quantity of 10–70 percent of the weight of water, and also in the presence of a catalyst; the result of this processing is a reaction mixture containing tertiary butyl alcohol and water; tertiary butyl alcohol is isolated from the reaction mixture as an aqueous solution which is dehydrated at a temperature of 80°–110° C and a pressure not above 3 atm in the presence of the said catalyst.

According to the invention, the catalyst used in processing the $C_4$ hydrocarbon fractions, and also in dehydration of tertiary butyl alcohol, is a moulded ion-exchange catalyst consisting of sulphonated copolymer of styrene with divinylbenzene, or diisopropenylbenzene, and a sulphonated thermoplastic material, taken in the weight ratio of 1 – 4: 1–2 respectively.

The $C_4$ hydrocarbon fraction is, for example one obtained in pyrolysis of petrol and other petroleum products, in dehydrogenation of isobutane, and in cracking petroleum products. These fractions contain 20–50 percent by weight of isobutylene. As these fractions are processed with water in the selected conditions, isobutylene is hydrated. The hydrocarbon fraction and water are taken at a molar ratio of 1:5–20. Lower ratio decreases conversion of isobutylene and increases the yield of side products. At higher ratio, the concentration of tertiary butyl alcohol decreases. The preferable molar ratio of the hydrocarbon fraction to water is 1:10. The conditions of the hydration process should ensure maximum conversion of isobutylene into tertiary butyl alcohol and the maximum production capacity of the process. This is ensured in that the process is realized in a liquid phase at a temperature of 70°–110° C and a pressure of 16–23 atm., in the presence of moulded ion-exchange catalyst. It is not recommended to carry out the process at low temperatures, since the rate of the reaction of isobutylene hydration decreases. At increased temperatures the equilibrium of the hydration reaction is shifted in the direction of formation of the starting products. Moreover, this involves elevated pressures that are necessary to maintain the components in the liquid state. The selected ion-exchange catalyst has highly developed inner surfaces and high porosity. The static ion-exchange capacity of this catalyst is 3–4.25 mg-equiv. per gram of the dry substance.

Hydrocarbons are known to be practically insoluble in water. Therefore, if the hydration of isobutylene is carried out in the absence of substances that dissolve both water and hydrocarbons, the conversion degree of isobutylene will be lowered, and the production capacity decreased too, and that is why the process is carried out in the presence of a polar solvent capable of dissolving water and hydrocarbons: ethyl-cellosolve, dioxane, n-propanol, acetone, etc. The solvent is taken in the quantity of 10 – 70 percent of the weight of water (depending on its power to dissolve said reagents).

As a result of processing of the $C_4$ hydrocarbon fractions with water under the selected conditions, a reaction mixture is formed, that contains tertiary butyl alcohol and water. In order to ensure high production capacity of the process of dehydration of tertiary butyl alcohol into isobutylene, and to obtain isobutylene of high purity, it is necessary to remove unreacted hydrocarbons from the obtained reaction mixture. The mixture is then rectified to prepare a concentrated aqueous solution of tertiary butyl alochol containing dissolved low-boiling hydrocarbons. These latter substances are removed by distilling. The resultant aqueous solution of tertiary alcohol has the concentration of 85–88 percent.

The reaction of tertiary butyl alcohol dehydration is reversible, and water and isobutylene can be thus obtained. The conditions of this process are therefore so selected that the equilibrium of the reaction should be shifted in the direction of formation of the wanted products. These conditions are as follows: temperature 80°–110° C, pressure not above 3 atm, and also the presence of the above named catalyst.

The selected moulded ion-exchange catalyst consists of a sulphonated copolymer of styrene and divinylbenzene, or diisopropenylbenzene and a sulphonated thermoplastic material. The sulphonated thermoplastic material is sulphonated polyethylene, sulphonated polypropylene, or sulphonated polyvinylchloride.

It has already been said that the $C_4$ hydrocarbon fractions are processed with water in the presence of a polar solvent. If the solvent is taken in insufficient quantity, hydrocarbon and aqueous layers are formed. In this case, to the mixture of the $C_4$ hydrocarbon fraction, water, and the polar solvent, should be added an emulsifying agent in the quantity of 0.3–2 percent of the weight of water. The presence of an emulsifying agent ensures homogeneity of the system. Non-ionic-substances, such as hydroxyethylated higher fatty alcohols, hydroxyethylated alkylphenols, and cation-active emulsifying agents, such as n-dodecylpyridinium chloride, n-dodecyltrimethylammonium chloride, are used as the emulsifying agents.

The above described moulded ion-exchange catalyst is characterized by high catalytic activity, which is 50–100 percent higher than that of the sulphocationites. The catalyst is also characterized by high thermal stability. It does not, practically, lose its catalytic properties for 4000–4500 hours of operation at temperatures of the order to 85°–100° C. This makes it possible to increase the production capacity of the process 1.5–2 times compared with the known method for separation of isobutylene with sulphocationites. The space velocity of delivery of the mixture of the starting components increases from 1.5–2 hour$^{-1}$ to 3 hour$^{-1}$. The moulded ion-exchange catalyst is used, for example, in the form of small cylinders or rings. The bed of this catalyst produces only insignificant resistance to the flow of the reactants. This, in turn, makes it possible to arrange the catalyst in beds as high as 4.5 m each, while in the known method the height of the catalyst bed is only 2 meters. Moreover, the proposed catalyst has high mechanical strength, which is 200 kg/sq.cm. Such phenomena as mechanical attrition, or washing out of the catalyst, are absent. Owing to this quality of the catalyst, the process can easily be realized on an industrial scale.

The proposed method can be realized as follows.

The $C_4$ hydrocarbon fraction is mixed with water at a molar ratio of 1 : 5–20, in the presence of a polar solvent, for example, ethyl 'Cellosolve', or dioxane. The polar solvent is taken in the quantity of 10–70 percent of the weight of water. If the polar solvent is taken in the quantity of 10–50 percent of the weight of water, cation-active or non-ionic emulsifying agent should be added to the obtained mixture in the quantity of 0.3–2 percent of the weight of water. The mixture is delivered into the hydrator vessel at a space velocity of 2–3 hour$^{-1}$. The linear velocity of the liquid flow through the reactor is to 50 m/hour. The moulded ion-exchange catalyst is placed in the hydrator on gauzes in beds (one or more). The height of one such bed is to 4 meters and a half. Isobutylene is hydrated into tertiary butyl alcohol in the hydrator at a temperature of 70°–110° C, preferably at 85°–90° C, and at a pressure of 16–23 atm. The process occurs in the liquid phase. The degree of isobutylene conversion is practically 93–97 percent. The reaction mixture containing tertiary butyl alcohol and water is delivered into an intermediate vessel to remove unreacted hydrocarbons by evaporation, and then is rectified to prepare concentrated aqueous solution of tertiary butyl alcohol containing dissolved low-boiling hydrocarbons, which are removed by distillation. The result is an aqueous solution of tertiary butyl alcohol having the concentration of 75–88 percent. The aqueous solution of alcohol is delivered to the dehydration reactor which is a vertical cylindrical apparatus consisting of the rectification and reaction sections. The upper part is the reaction section, filled with moulded ion-exchange catalyst. The catalyst is arranged here in the same manner as in the hydrator. The lower part of the apparatus, the rectification section, is filled with cap trays. The aqueous solution of tertiary butyl alcohol is delivered into the reaction section of the apparatus, under the catyst bed, at a space velocity of 0.3–0.75 hour$^{-1}$. At a temperature of 80°–110° C and a pressure not above 3 atm., tertiary butyl alcohol is dehydrated into isobutylene, which is in the form of gas containing admixtures of vapours of unreacted tertiary butyl alcohol. It is delivered into a partial condenser and withdrawn from the system. Alcohol is condensed and delivered back into the upper part of the reactor. The linear velocity of gas and vapour in the reaction section of the dehydrator is 0.4 m/sec. The other product of dehydration, water, also containing admixtures of tertiary butyl alcohol, is delivered into the rectification section of the apparatus from which tertiary butyl alcohol in the form of vapour is delivered into the reaction section of the reactor, while water is discarded from the system. The degree of conversion of tertiary butyl alcohol is 99–100 percent.

For a better understanding of the invention, the following examples of its practical embodiment are given by way of illustration.

EXAMPLE 1

A reactor, which is a steel tube, 1.5 m long and 10 mm inner diameter, provided with a thermostatting jacket, is loaded with 30 g (120 cc) of moulded ion-exchange catalyst. The catalyst is 5×5 mm cylinders of a sulphonated copolymer of styrene with divinylbenzene (70 parts by weight), and sulphonated polyethylene (30 parts by weight). The static exchange capacity of the catalyst is 3.9 mg-equiv./g of dry catalyst. A mixture of isobutane-isobutylene fraction, containing 40 percent of isobutylene, and an aqueous solution of ethyl 'Cellosolve', having the concentration of 50 percent, containing 1 percent (of the weight of water) of the emulsifying agent-hydroxyethylated higher fatty alcohols (fractions $C_{10}$–$C_{18}$), is delivered continually into the reactor. The molar ratio of the hydrocarbon fraction to water is 1:10, the rate of delivery of the mixture is 240 ml/hour (2.0 hour$^{-1}$). The pressure inside the reactor is maintained at 20 atm, and the temperature at 90° C. At the step of isobutylene hydration, the degree of its conversion into tertiary butyl alcohol is 93 percent.

The obtained reaction mixture containing tertiary butyl alcohol and water is delivered into an intermediate vessel where unreacted hydrocarbons are removed by evaporation, after which it is delivered for rectification. An aqueous solution of tertiary butyl alcohol containing dissolved low-boiling hydrocarbons is obtained as a result of rectification. The volatile substances are removed by distillation to obtain an aqueous solution of butyl alcohol having the concentration of 85 percent, which is then dehydrated.

Tertiary butyl alcohol is dehydrated in a column reactor having a diameter of 30 mm. The reactor consists of two parts, the lower, 500 mm high, working as a rectification column, and the upper part, the reaction section, 170 mm high. The lower part of the column is packed with nichrome wire, and the upper section with a catalyst taken in the quantity of 30 g (120 cc). The catalyst is the same as at the hydration step. The reactor is provided with a heater and a partial condenser.

The aqueous solution of tertiary butyl alcohol is delivered continually into the middle part of the reactor in the zone beneath the catalyst bed, at a rate of 50 ml/hour (0.4 hour$^{-1}$). The reaction temperature in this zone is maintained at 85°–87° C, the pressure 0.7 atm. The formed gaseous isobutylene, together with the vapour of unreacted tertiary butyl alcohol, rise into the partial condenser, where tertiary butyl alcohol is condensed and is again delivered onto the catalyst. Isobutylene is withdrawn (also continuously) from the system, condensed, and purified by rectification.

The other dehydration product — water containing admixture of tertiary butyl alcohol — is also delivered into the rectification section of the apparatus, from which tertiary butyl alcohol, in the form of vapour, is delivered into the reaction section of the apparatus, while water is withdrawn from the system.

The degree of tertiary butyl alcohol conversion is 100 percent. The concentration of isobutylene in the obtained product is 99.95 percent.

EXAMPLE 2

The reactor described in Example 1 is loaded with 30g (120 cc) of ion-exchange moulded catalyst, which is shaped in cylinders sizing 5×5 mm and consists of sulphonated copolymer of styrene with divinyl benzene (70 parts by weight) and sulphonated polypropylene (30 parts by weight). The static ion-exchange capacity of the catalyst is 3.9 mg-equiv./g of dry catalyst. A mixture of the $C_4$ hydrocarbon fraction containing 95.5 percent of isobutylene, and an aqueous solution of dioxane having the concentration of 50 percent, containing 2 percent of the emulsifying agent n-dodecyl-pyridinium chloride (with respect to the weight of water), is delivered continuously into the reactor. The molar ratio of the hydrocarbon fraction to water is 1:20. The rate of delivery of the mixture is 360 ml/hour (3.0 hour$^{-1}$). The pressure inside the reactor is 16 atm, the temperature 75° C. The degree of isobutylene conversion into tertiary butyl alcohol is 97 percent.

Tertiary butyl alcohol is isolated from the reaction mixture by the same procedure as described in Example 1. An aqueous solution of tertiary alcohol having the concentration of 88 percent is obtained as a result.

Tertiary butyl alcohol is dehydrated in the reactor, as described in Example 1. The catalyst (and also its quantity) used at the dehydration process, are the same as at the hydration step in Example 2. The procedure is similar to that described in Example 1, except that the rate of delivery of the aqueous solution of tertiary butyl alcohol is 45 ml/hour (0.37 hour$^{-1}$), the temperature in the reaction zone is maintained at 80° C, and the pressure is atmospheric.

The degree of tertiary butyl alcohol conversion is 99 percent. The concentration of isobutylene in the obtained product is 99.98 percent.

EXAMPLE 3

The reactor described in Example 1, is loaded with 36 g (120 cc) of the moulded ion-exchange catalyst, which is actually sulphonated copolymer of styrene with diisopropenyl benzene (45 parts by weight) and sulphonated polyvinyl chloride (55 parts by weight) shaped into 5 mm high and 3 mm in dia cylinders. The static ion-exchange capacity of the catalyst is 3.45 mg-equiv/g of dry catalyst.

A mixture of the $C_4$ hydrocarbon fraction isolated from the products of petrol pyrolysis, and containing 42.5 percent of isobutylene, and an aqueous solution of ethyl-cellosolve having the concentration of 70 percent, is delivered in a continuous flow into the reactor. The molar ratio of the hydrocarbon fraction to water is 1:10. The rate of the mixture delivery is 260 ml/hour (2.2 hour$^{-1}$). The pressure inside the reactor is 18 atm, the temperature 85° C. The degree of isobutylene conversion into tertiary butyl alcohol is 92.5 percent. Tertiary butyl alcohol is isolated from the reaction mixture by the same method as described in Example 1. The resultant aqueous solution of tertiary butyl alcohol has the concentration of 85 percent.

Tertiary butyl alcohol is dehydrated in the reactor described in Example 1. The catalyst used for dehydration is the same (and in the same quantity) as at the hydration step of Example 3. The procedure is the same as described in Example 1.

The concentration of isobutylene in the resultant product is 99.95 percent.

EXAMPLE 4

The reactor described in Example 1, is loaded with 38 g (120 cc) of an ion-exchange catalyst. The catalyst is a sulphonated copolymer of styrene with divinylbenzene (33 parts by weight) and sulphonated polyvinyl chloride (67 parts by weight) shaped into cylinder having 5 mm in diameter and 5 mm high. The static ion-exchange capacity of the catalyst is 2.7 mg-equiv/g of dry catalyst.

Into the reactor, continually fed is a mixture of the $C_4$ hydrocarbon fraction, similar to that described in Example 3, and an aqueous solution of ethyl-cellosolve, having the concentration of 50 percent, and containing 1 percent (of the weight of water) of the emulsifying agent hydroxyethylated higher fatty alcohols (fractions $C_{10}$–$C_{18}$). The molar ratio of the hydrocarbon fraction to water is 1:10; the rate of feed is 260 ml/hour (2.2 hour$^{-1}$). The temperature in the reaction zone is 90° C, the pressure 20 atm. The degree of isobutylene conversion into tertiary butyl alcohol is 92 percent.

Tertiary butyl alcohol is isolated from the reaction mixture by a procedure similar to that described in Example 1. The resultant product is an aqueous solution of tertiary butyl alcohol having the concentration of 85 percent.

Tertiary butyl alcohol is dehydrated in the reactor described in Example 1. The catalyst used for the dehydration process is the same (and also taken in the same quantity) as at the hydration step. The procedure is the same as in Example 1, except that tertiary butyl alcohol is delivered at a rate of 40 ml/hour (0.33 hour$^{-1}$). The degree of tertiary butyl alcohol conversion is 99 percent.

The concentration of isobutylene in the obtained product is 99.95 percent.

EXAMPLE 5

The reactor described in Example 1 is loaded with 30 g (120 cc) of ion-exchange catalyst, which is a sulphonated copolymer of styrene with divinylbenzene (80 parts by weight) and sulphonated polypropylene (20 parts by weight) moulded into 5 × 5 mm cylinders. The static ion-exchange capacity of the catalyst is 4.25 mg-equiv/g of dry catalyst. Into the reactor, continually fed is a mixture of isobutane-isobutylene fraction containing 40 percent of isobutylene, and an aqueous solution of n-propyl alcohol, having the concentration of 30 percent, containing 2 percent (of the weight of water) of the emulsifying agent hydroxyethylated higher fatty alcohols (fraction $C_{10}$–$C_{18}$). The molar ratio of the hydrocarbon fraction to water is 1:10. The rate of feed is 330 ml/hour (2.75 hour$^{-1}$). The pressure inside the reaction zone reactor is maintained at 23 atm, the temperature is 105° C. The degree of isobutylene conversion into tertiary butyl alcohol is 92 percent.

Tertiary butyl alcohol is isolated from the reaction mixture by a procedure similar to that described in Example 1. The obtained aqueous solution of tertiary butyl alcohol has the concentration of 85 percent.

Tertiary butyl alcohol is dehydrated as described in Example 1. The catalyst used at the dehydration step is the same (and taken in the same quantity) as at the hydration step. The degree of tertiary butyl alcohol conversion is 99 percent. The concentration of isobutylene in the obtained product is 99.95 percent.

EXAMPLE 6

The reactor described in Example 1 is loaded with 30 g (120 cc) of ion-exchange catalyst which is the same as described in Example 2.

Into the reactor, continually fed is a mixture of the $C_4$ hydrocarbon fraction isolated from petrol pyrolysis products and containing 28.7 percent of isobutylene, and an aqueous solution of ethyl-cellosolve, having the concentration of 50 percent, containing 2 percent (of the weight of water) of the emulsifying agent hydroxyethylated alkylphenols (alkyl contains from 7 to 10 carbon atoms). The molar ratio of the hydrocarbon fraction to water is 1:5. The rate of feed is 300 ml/hour (2.5 hour$^{-1}$). The pressure inside the reactor is 20 atm, the temperature is 90° C. The degree of isobutylene conversion into tertiary butyl alcohol is 92 percent.

Tertiary butyl alcohol is isolated from the reaction mixture by a procedure similar to that described in Example 1.

Tertiary butyl alcohol is dehydrated in the reactor described in Example 1. The catalyst used at the dehydration step is the same (and also taken in the same quantity) as at the hydration step of the process. The procedure is the same as in Example 1, except that the solution of tertiary butyl alcohol is delivered at a rate of 90 ml/hour (0.75 hour$^{-1}$), the pressure in the reactor is 1.5 atm, and the temperature is 100°–105° C. The degree of tertiary butyl alcohol conversion is 99 percent. The concentration of isobutylene in the obtained product is 99.95 percent.

EXAMPLE 7

A reactor, which is a 9-m high steel cylinder, having the inner diameter of 0.147 m, is loaded with 33 kg (130 liters) of ion-exchange catalyst arranged in two beds. The catalyst is a sulphonated copolymer of styrene with divinylbenzene (70 parts by weight), and sulphonated polypropylene (30 parts by weight). The static ion-exchange capacity of the catalyst moulded into cylinders 5–10 mm high and 4–5 mm in diameter is 3.9 mg-equiv/g of dry catalyst. Into the reactor, fed continually is a mixture of the $C_4$ hydrocarbon fraction isolated from the petrol pyrolysis products, and containing 42.5 percent of isobutylene, and an aqueous solution of ethyl-cellosolve having the concentration of 50 percent, containing 1 percent (of the weight of water) of the emulsifying agent hydroxyethylated higher fatty alcohols (fraction $C_{10}C_{18}$). The molar ratio of the hydrocarbon fraction to water is 1:10, the rate of feed is 260 l/hour (2.0 hour$^{-1}$). The pressure inside the reactor is 18 atm, the temperature 85°–100° C. The degree of isobutylene conversion into tertiary butyl alcohol is 93 percent.

Tertiary butyl alcohol is isolated from the reaction mixture by a procedure similar to that described in Example 1. The resultant aqueous solution of tertiary butyl alcohol has the concentration of 75 percent.

Tertiary butyl alcohol is dehydrated in the column-type reactor having the inner diameter of 0.250 m. The reactor consists of two parts, the lower section, rectification column, 4 meters high, and the upper part, the reaction section, 4.5 m high. The lower, rectification section, is packed with 12 cap trays. The upper part of the apparatus is filled with the catalyst, which is the same as at the hydration step of the process. The catalyst charge is 50 kg (200 liters).

The reactor is provided with a heater and a partial condenser.

The process is carried out by a procedure similar to that described in Example 1, except that the rate of feed of the aqueous solution of tertiary butyl alcohol is 200 liters per hour (1.0 hour$^{-1}$), the temperature in the reaction zone is 85°–87° C, and the pressure is 0.5–0.7 atm. The degree of tertiary butyl alcohol conversion is 99 percent. The concentration of isobutylene in the obtained product is 99.95%.

EXAMPLE 8

A reactor, which is a 12-m high steel cylinder having the inner diameter of 3.8 m, is loaded with 32 tons (80 c.m.) of ion-exchange catalyst as described in Example 7. The catalyst is arranged in the column in two beds, each bed 4.5-m high. Into the reactor, fed continuously is a mixture of the $C_4$ hydrocarbon fraction and an aqueous solution of ethyl-cellosolve, having the composition similar to that described in Example 6. The hydration process is carried out in the same conditions as in Example 7, except that the rate of feed of the mixture is 160 cu.m/hour. The degree of isobutylene conversion into tertiary butyl alcohol is 92 percent.

Tertiary butyl alcohol is isolated from the reaction mixture by the procedure described in Example 1. The obtained aqueous solution of tertiary butyl alcohol has the concentration of 75 percent.

Tertiary butyl alcohol is dehydrated in a column-type reactor consisting of two parts, — the lower part, which is a rectification column, and the upper, reaction section. The diameter of the lower part is 2 meters, the height is 7 m. The diameter of the upper part is 4 m, the height 5 m. The lower part is packed with 12 trays, and the upper part of the apparatus is filled with a catalyst, which is the same as at the hydration step. The catalyst charge is 32 tons (80 cu.m). The dehydration conditions are the same as described in Example 7, except that the rate of feed of the aqueous solution of tertiary butyl alcohol is 5,500 kg/hour (0.7 hour$^{-1}$). The degree of tertiary butyl alcohol conversion is 99 percent. The concentration of isobutylene in the obtained product is 99.95 percent.

What is claimed is:

1. A method for separating high-purity isobutylene from $C_4$ hydrocarbon fractions which comprises treating said fractions with water at a temperature of from 70° to 110° C, under a pressure of from 16 to 23 atm., and a hydrocarbon fraction-to-water molar ratio being 1:5–20, in the presence of a polar solvent capable of dissolving both water and hydrocarbon in an amount of from 10 to 70% of the water weight and in the presence of an ion-exchange molded catalyst comprising a sulfonated styrene-divinylbenzene or di-isopropenylbenzene copolymer and a sulfonated thermoplastic material selected from the group consisting of sulfonated polyethylene, sulfonated polypropylene and sulfonated polyvinyl chloride, the sulfonated copolymer-to-sulfonated thermoplastic material weight ratio in said catalyst being equal to 1–4:1–2, respectively, whereby the isobutylene is converted to tert.butyl alcohol, followed by separating the hydrocarbon fraction from the tert.butyl alcohol solution, and thereafter dehydrating the tert.butyl alcohol to isobutylene at a temperature of from 80° to 110° C, under a pressure of 3 atm. maximum, and in the presence of said catalyst.

2. A method according to claim 1 wherein the treatment of $C_4$ hydrocarbon fractions with water is conducted in the presence of an emulsifying agent selected from the group consisting of hydroxyethylated higher fatty alcohols, hydroxyethylated alkylphenols and n-dodecylpyridinium chloride, said emulsifying agent being taken in an amount of 0.3–2% of the water weight.

* * * * *